United States Patent [19]

Hilton

[11] Patent Number: 4,493,994
[45] Date of Patent: Jan. 15, 1985

[54] DETECTING THE CONDITION OF A SHEET

[75] Inventor: Graham H. Hilton, Lovedean, England

[73] Assignee: De La Rue Systems Limited, London, England

[21] Appl. No.: 436,920

[22] Filed: Oct. 27, 1982

[30] Foreign Application Priority Data

Oct. 27, 1981 [GB] United Kingdom ............... 8132363

[51] Int. Cl.³ ............................................. G01V 9/04
[52] U.S. Cl. ............................ 250/223 R; 250/572; 250/562; 209/534
[58] Field of Search ............... 250/572, 223 R, 562, 250/563; 356/430, 237; 209/534; 226/45, 88; 73/587

[56] References Cited

U.S. PATENT DOCUMENTS

| 3,656,615 | 4/1972 | Ptacek | 209/534 |
| 4,099,884 | 7/1978 | Nash | 250/572 |
| 4,463,607 | 8/1984 | Hilton | 73/587 |

Primary Examiner—Davis L. Willis
Assistant Examiner—J. Gatto
Attorney, Agent, or Firm—Sughrue, Mion, Zinn, Macpeak and Seas

[57] ABSTRACT

A method of detecting the condition of a rectangular sheet (8), comprising feeding the sheet, e.g. by belts (2, 4), through a checking station (adjacent to II—II), the direction of feeding (6) being along the length or the width of the sheet; deflecting, e.g. by stationary guide rails (10a, 12a), a portion of a side edge of the sheet at the checking station relatively to the remainder of a zone of the sheet (8) lying adjacent to a line through the checking station transverse to the direction of feeding, the direction of deflection of the deflected portion being orthogonal to the line and to the direction of feeding, so that the deflected portion is stretched along the direction of feeding; and subjecting the deflected portion to a beam of radiation directed from means (14a) towards sensing means (16a) and intercepted by the deflected portion, whereby any substantial tear from the side edge into the deflected portion will be opened, and will be revealed by the sensing means receiving radiation through the opened tear.

5 Claims, 4 Drawing Figures

DETECTING THE CONDITION OF A SHEET

This invention relates to methods and apparatus for detecting the condition of a rectangular sheet, and is primarily applicable to paper sheets, and especially to all types of security document, e.g. banknotes, travellers cheques, and vouchers. For simplicity, banknotes will be used as an example later in this specification.

Banknotes which have been in circulation may be worn or damaged in various ways, and one type of damage is tearing into the edges, especially into the longitudinal edges. It is desirable to detect this type of damage, because it may interfere with mechanical handling of a banknote.

According to the present invention, a method of detecting the condition of a rectangular sheet comprises feeding the sheet through a checking station, the direction of feeding being along the length or the width of the sheet; and is characterised by: deflecting a portion of a side edge of the sheet at the checking station relatively to the remainder of a zone of the sheet lying adjacent to a line through the checking station transverse to the direction of feeding, the direction of deflection of the deflected portion being orthogonal to the line and to the direction of feeding, so that the deflected portion is stretched along the direction of feeding; and subjecting the deflected portion to a beam of radiation directed towards sensing means and intercepted by the deflected portion, whereby any substantial tear from the side edge into the deflected portion will be opened, and will be revealed by the sensing means receiving radiation through the opened tear.

Conveniently the radiation is visible light, but other wavelengths can be used, particularly the infra-red. For simplicity, visible light will be used as an example later in this specification.

In practice, a plurality of sheets can be fed in succession through the checking station, and the result will be that the sensing means will record darkness while an undamaged sheet is passing, will record darkness plus a flash of light when a sheet with a substantial tear is passing, and will record light during the intervals between the passage of one sheet and the next. Such an output from sensing means can be used to control the subsequent distribution of the sheets to two receivers, one for sheets in good condition and one for sheets in poor condition.

Preferably the sheet is fed at uniform speed through the checking station, and the deflection progresses continuously along the side edge as the sheet passes the checking station.

Preferably the condition of two side edges of a sheet is detected at the same time, that is to say two opposite side edges of the sheet are deflected at the checking station, and are subjected to respective light beams.

In practice the invention is of primary interest in relation to the condition of the longer sides of a sheet, the direction of feeding of the sheet being along the length of the sheet. Tears close to a corner of the sheet may not be detected.

Preferred apparatus according to the present invention comprises a pair of opposed belts, means for loading a sheet into a position in which the belts grip a zone of the sheet extending centrally along the length or the width of the sheet; driving means such that the belts can carry the sheet through a checking station, while moving in the direction of the said length or width; stationary guide rails extending through the checking station and shaped to guide the side edges of the sheet along sinuous paths; means at the checking station directing a beam of radiation at a portion of each side edge; and sensing means to receive each beam when not intercepted by the respective side edge of the sheet.

The accompanying diagrammatic drawings illustrate one embodiment of such preferred apparatus. In these drawings.

The apparatus shown in FIGS. 1 and 2 will be described first.

Banknotes are conveyed in succession, from a supply (not shown, but see the later description of FIG. 4), by means of a pair of opposed belts 2, 4. The direction of feed is indicated by the arrow 6 in FIG. 1. The position of a banknote while passing through the apparatus is indicated by the chain line 8, the length of the banknote being L and the width being W. This particular apparatus is intended to handle U.S. dollar bills, which are 155 mm long and 66 mm wide in all denominations.

The belts 2, 4 grip a central longitudinal zone of the banknote. In FIGS. 1 and 2, for the sake of clarity, the opposed runs of the belt are shown spaced slightly apart; in practice they are pressed together in order to grip the banknotes. The belts 2, 4 are 12 mm wide, and lie in adjacent parallel planes, so that the banknotes are held in a flat condition, apart from the local deflection of the side edges as described later.

Figure 1:
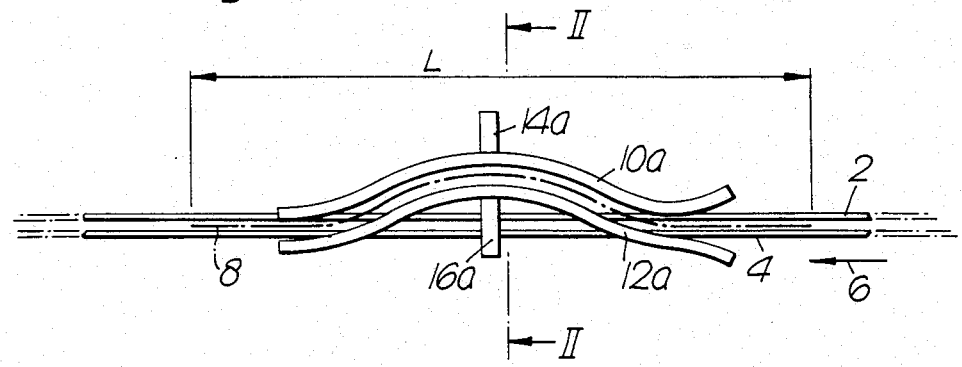
FIG. 1 is a diagrammatic side elevation, looking in the direction of the arrow I in FIG. 2.
Figure 2:
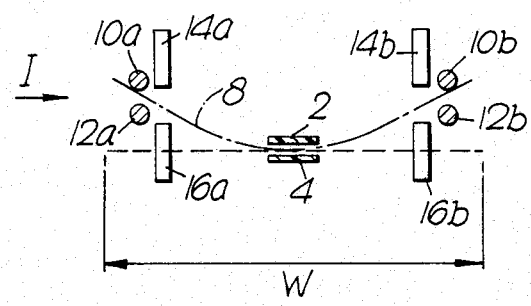
FIG. 2 is a diagrammatic cross section in the plane II—II in FIG. 1.

A checking station lies immediately to the left of the plane of section II—II in FIG. 1 and is seen in FIG. 2. Passing through the checking station are pairs of stationary guide rails 10a, 12a; 10b, 12b. As is apparent from FIG. 1, these guide rails are shaped to guide the side edges of the banknote along sinuous paths, the curves of which are in planes perpendicular to the plane of the central zone of the sheet. The result is to deflect the banknote as shown by the chain lines 8 in FIGS. 1 and 2, with the consequence that, at any given moment in time, a portion of each side edge of the banknote is deflected and consequently is stretched longitudinally of the sheet. The consequence of this stretching is that any substantial tear in the side edge will be opened, so that light can pass through it. This is in contrast to the situation when the banknote is flat; then a tear may be completely closed, so that substantially no light would pass through it.

In the example shown, the length of the sinuous part of each of the guide rails 10a, 12a, 10b, 12b is 50 mm and the vertical deflection of the mid point of each guide rail is 10 mm.

At the checking station, and adjacent to each pair of guide rails, is a light source 14a, 14b and an optical sensor 16a, 16b. The distance between centres of the sensors 16a, 16b is 45 mm.

Figure 3:
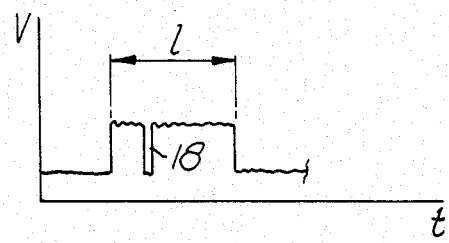
FIG. 3 is a diagram of the output from a sensor during the passage of one damaged banknote.

FIG. 3 is a diagram of the output of a sensor (in volts V) plotted against time (t). When the light beam from the associated source reaches the sensor, the output has a low level, while when the light beam is obstructed by a side edge portion of a banknote, the output has a higher value. The period of time marked 1 corresponds to the passing of the length of a banknote. If the banknote has no tear in the side edge in question, then the output is continuously high during the time l. If, on the other hand, there is a tear, this is revealed by a brief downward pulse in output indicated at 18.

In practice a tear shorter than about 12 mm may not be detected, and a tear at about 50 mm or less from a corner of the banknote, especially at less than 25 mm from a corner, may not be detected.

The outputs from the sensors 16a and 16b can be handled by a circuit which controls means (not shown) for directing banknotes, after leaving the belts 2, 4, to two alternative receivers, one for banknotes in good condition, and one for banknotes in poor condition.

FIGS. 1 and 2 show the light sources 14a, 14b and the sensors 16a, 16b as being slightly nearer than the guide rails to the centre line of the belts 2, 4. However, the light sources and sensors may alternatively be slightly further than the guide rails from the centre line.

Figure 4:
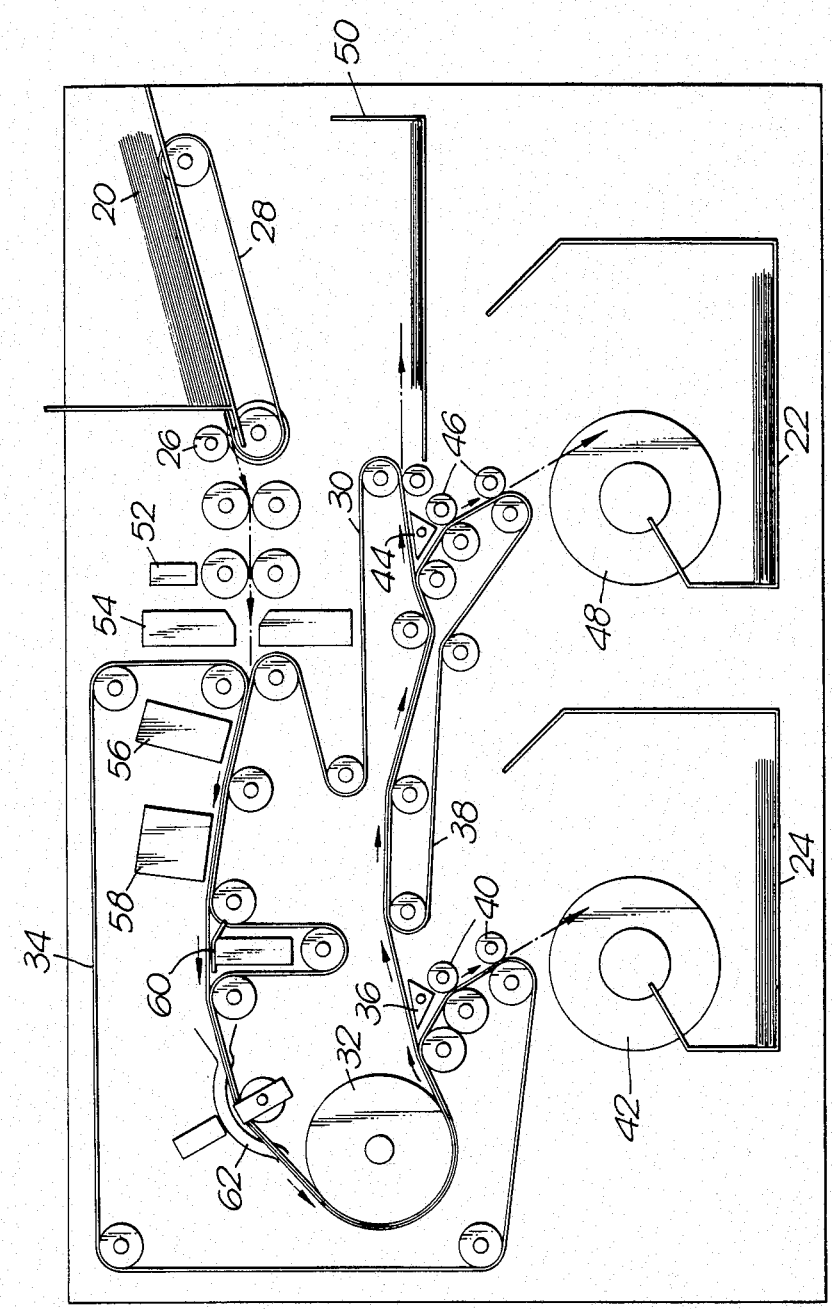
FIG. 4 is a diagram of the layout of one machine in which the apparatus can be incorporated.

FIG. 4 is a diagram of the layout of one machine in which the apparatus described above can be incorporated. The machine serves to sort fit banknotes from unfit banknotes.

Unsorted banknotes are placed in a feed hopper 20. Fit notes are delivered to a stack at 22 while unfit notes are delivered to a stack at 24. Notes which are overlapping or folded are rejected to a cull pocket 50 for subsequent further treatment.

A feed roller 26 and feed belt 28 serve to remove notes one by one from the bottom of the feed hopper 20, so that the notes then travel along a gently and smoothly curved path defined by a belt 30 driven by a capstan 32, and a cooperating belt 34. The notes pass various inspecting stations, which will be described more fully below, and as a consequence each note becomes associated with a signal indicating that the respective note is either fit or unfit. This signal controls a diverter station 36, by means of which the note is directed either to a second belt 38 cooperating with the driven belt 30, or is directed downwards past rollers 40 to a stacking wheel 42 associated with the unfit note stack 24.

Notes conveyed by the belts 38 and 30 reach a second diverter station 44, from which they proceed either downwards past rollers 46 to a stacking wheel 48 associated with the fit note stack 22, or horizontally to the cull pocket 50.

As each note proceeds from the feed roller 26, it first passes a thickness measuring sensor at 52. This serves to detect overlapping notes and folded notes. A signal from this sensor 52 controls the second diverter station 44.

Each note then passes in succession:
a holes and tears sensor at 54;
an ultra violet fluorescent sensor 56;
a magnetic ink sensor 58.

Next, each note passes a sensor 60 which determines the stiffness of the note, either by its reflective condition, or by a noise emitted by the note when bent. Low stiffness is an indication of wear. Apparatus for determining stiffness by noise is described in my U.S. patent application Ser. No. 409,213.

Finally the note passes at 62 a sensor as described above with reference to FIGS. 1 and 2. (The belts 34, 30 correspond to the belts 2, 4 in FIGS. 1 and 2).

After leaving the sensor 62, the note passes the drive capstan 32, and arrives at the diverter station 36.

I claim:

1. A method of detecting the condition of a rectangular sheet, comprising: feeding the sheet through a checking station, the direction of feeding being along the length or the width of the sheet; deflecting a portion of a side edge of the sheet at the checking station relatively to the remainder of a zone of the sheet lying adjacent to a line through the checking station transverse to the direction of feeding, the direction of deflection of the deflected portion being orthogonal to the line and to the direction of feeding, so that the deflected portion is stretched along the direction of feeding; and subjecting the deflected portion to a beam of radiation directed towards sensing means and intercepted by the deflected portion, whereby any substantial tear from the side edge into the deflected portion will be opened, and will be revealed by the sensing means receiving radiation through the opened tear.

2. A method according to claim 1, in which the feeding of the sheet is at uniform speed through the checking station, whereby the deflection progresses continuously along the side edge as the sheet passes the checking station.

3. A method according to claim 1, comprising deflecting two opposite side edges of the sheet at the checking station, and subjecting the side edges to respective beams of radiation.

4. A method according to claim 3, including maintaining a longitudinal central zone of the sheet in a plane or smooth curve during feeding, while guiding the side edges along respective sinuous paths.

5. Apparatus for detecting the condition of a rectangular sheet, comprising: a pair of opposed belts; means for loading a sheet into a position in which the belts grip a zone of the sheet extending centrally along the length or the width of the sheet; driving means such that the belts can carry the sheet through a checking station, while moving in the direction of the said length or width; stationary guide rails extending through the checking station and shaped to guide the side edges of the sheet along sinuous paths; means at the checking station directing a beam of radiation at a portion of each side edge; and sensing means to receive each beam when not intercepted by the respective side edge of the sheet.

* * * * *